United States Patent
Hommann et al.

(10) Patent No.: US 9,155,836 B2
(45) Date of Patent: Oct. 13, 2015

(54) INJECTION DEVICE WITH A SPRING FOR A NEEDLE PROTECTING SLEEVE

(76) Inventors: Edgar Hommann, Grossaffoltern (CH); Benjamin Scherer, Uster (CH); Ian Thompson, Burgdorf (CH)

( * ) Notice: Subject to any disclaimer, the term of this patent is extended or adjusted under 35 U.S.C. 154(b) by 560 days.

(21) Appl. No.: 12/644,304

(22) Filed: Dec. 22, 2009

(65) Prior Publication Data
US 2010/0191217 A1 Jul. 29, 2010

Related U.S. Application Data

(63) Continuation of application No. PCT/CH2008/000288, filed on Jun. 26, 2008.

(30) Foreign Application Priority Data

Jun. 29, 2007 (DE) .................. 10 2007 030 327

(51) Int. Cl.
*A61M 5/20* (2006.01)
*A61M 5/24* (2006.01)
*A61M 5/32* (2006.01)

(52) U.S. Cl.
CPC ............... *A61M 5/2033* (2013.01); *A61M 5/24* (2013.01); *A61M 5/326* (2013.01); *A61M 2005/206* (2013.01); *A61M 2005/208* (2013.01); *A61M 2005/2013* (2013.01); *A61M 2005/3247* (2013.01)

(58) Field of Classification Search
CPC ..... A61M 5/2033; A61M 5/24; A61M 5/326; A61M 2005/2013; A61M 2005/2026; A61M 2005/206; A61M 2005/208; A61M 2005/3247; A61M 2005/3263; A61M 2005/3265; A61M 2005/3267
USPC .......... 604/110, 130, 131, 134, 135, 187, 197, 604/198, 137
See application file for complete search history.

(56) References Cited

U.S. PATENT DOCUMENTS

2001/0037087 A1* 11/2001 Knauer ..................... 604/137
2005/0203466 A1* 9/2005 Hommann et al. ........ 604/240

FOREIGN PATENT DOCUMENTS

| DE | 10 2004060146 | 8/2004 |
|---|---|---|
| WO | WO 94/21316 | 9/1994 |
| WO | WO 2005/023341 | 3/2005 |
| WO | WO 2005/044344 | 5/2005 |
| WO | WO 2005/044347 | 5/2005 |

OTHER PUBLICATIONS

English Translation of WO 2005/044347 from EPO website. Translated Sep. 17, 2014.*

* cited by examiner

*Primary Examiner* — Kami A Bosworth
(74) *Attorney, Agent, or Firm* — Dorsey & Whitney LLP; Stuart R. Hemphill, Esq.

(57) ABSTRACT

An injection device including a housing, a needle guard sleeve displaceable relative to the housing, and a spring coupled to the guard sleeve such that the guard sleeve can be moved by the spring distally from a proximal position to an end position, the spring also being coupled to a forward drive element displaceable relative to the housing in a drive direction wherein the spring is tensioned upon a movement of the forward drive element in the forward drive direction.

17 Claims, 3 Drawing Sheets

INJECTION DEVICE WITH A SPRING FOR A NEEDLE PROTECTING SLEEVE

CROSS-REFERENCED RELATED APPLICATIONS

This application is a continuation of International Patent Application No. PCT/CH2008/000288 filed Jun. 26, 2008, which claims priority to German Patent Application No. 10 2007 030 327.2 filed Jun. 29, 2007, the entire contents of both of which are incorporated herein by reference.

BACKGROUND

The invention relates to devices for delivering, injecting, infusing, administering or dispensing a substance, and to methods of making and using such devices. More particularly, it relates to an injection device, such as an auto-injector, for injecting a fluid product, such as a drug for diabetes or insulin therapy, wherein, after the product has been successfully administered, a needle protecting sleeve associated with the injection device is moved or slid over the injection needle to protect against injury.

Moving or sliding a needle protecting sleeve over a needle in the distal (forward) direction, from its proximal (rearward) position in which the needle is exposed, by using a spring, such that the needle is protected against being accessed from without, is known from the prior art. The spring which charges the needle protection with a spring force is biased by an amount in the proximal position of the needle protecting sleeve. When the needle protecting sleeve is advanced beyond the injection needle, the spring force decreases according to the rules of Hooke's Law. The bias on the spring therefore has to be selected such that the needle protecting sleeve can reliably assume the end position in which it covers the injection needle.

Shifting the needle protecting sleeve from a distal position into the proximal position beforehand, to bias the spring, is also known. During this movement, mechanical switching processes of parts which are coupled to the needle protecting sleeve are performed as applicable. To effect these switching processes, additional forces which act on the needle protecting sleeve in the proximal direction are needed, in addition to the force needed to bias the spring, to shift the needle protecting sleeve in the proximal direction. It is, however, desirable to keep the total force needed to shift the needle protecting sleeve in the proximal direction low, to make it easier for the user to handle the device. On the other hand, as stated above, increased spring forces are desirable for shifting the needle protecting sleeve in the distal direction from the proximal position.

SUMMARY

It is therefore one object of the present invention to provide an injection device and a method in which the spring force driving the needle protecting sleeve can be adapted in accordance with the administering process.

In one embodiment, the present invention comprises an injection device comprising a housing, a needle guard sleeve displaceable relative to the housing, and a spring coupled to the guard sleeve such that the guard sleeve can be moved by the spring distally (forward) from a proximal (rear) position to an end position, the spring also being coupled to a drive element displaceable relative to the housing in a forward drive direction wherein the spring is tensioned upon a movement of the drive element in the forward drive direction.

In one embodiment, the present invention comprises an injection device for administering a fluid product. The fluid product can, for example, be insulin or a hormone or other drug. The injection device can be embodied as a simple injection device, e.g. an injection needle formed on or carried by the injection device is injected manually. Alternatively, the injection device can be embodied as an auto-injector, generally wherein the injection needle is injected by an injection mechanism, and wherein the product is delivered via a delivery mechanism once the injection needle has been injected.

In one embodiment, the present invention comprises an injection device with a housing. A needle guard sleeve, which is displaceable relative to the housing, is coupled to a spring in such a way that the needle guard sleeve can be moved distally from a proximal position to an end position with the spring. The spring is coupled to a forward drive element, which is displaceable relative to the housing, in such a way that it can be tensioned upon a movement of the forward drive element in the forward drive direction.

In some embodiments, the injection device comprises a housing. The housing can comprise one part or multiple parts, for example it may comprise a proximal housing part and a distal housing part which is latched, axially fixed, to the proximal housing part. A multiple-part housing offers advantages when assembling the injection device.

In some embodiments, the injection device also comprises an activating element which can be shifted relative to the housing and which may be thought of and/or referred to as a needle protecting sleeve or needle cover. The activating element can be able to be moved along the longitudinal axis of the housing which is, for example, cylindrical, between distal (forward) and proximal (rearward) positions. In some preferred embodiments, the activating element can at least be shifted from an activating position, e.g. a proximal position, in which the activating element is activated, in the distal direction, into an end position. In some preferred embodiments, the activating element can additionally be shifted proximally from an initial position into the activating position. The initial position and the end position can, but need not, be identical. In the end position, the activating element assumes a more distal position than in the initial position. In its end position, the activating element protrudes distally beyond the distal end of the housing, wherein for example the activating element protrudes distally beyond the distal end of the housing by a greater amount in its end position than in its initial position. When the activating element protrudes distally beyond the distal end of the housing, it simultaneously forms the distal end of the injection device. As applicable, the activating element also protrudes distally beyond the distal end of the housing in its initial position. It can, for example, be able to be moved from this position into the activating position.

In some preferred embodiments, the activating element in the end position protrudes beyond the distal end of the injection needle formed on the injection device. This prevents access to the injection needle and reduces the danger of injury. The activating element can also protrude beyond the distal end of the injection needle in the initial position. Alternatively, the distal end of the injection needle can protrude beyond the distal end of the activating element in the initial position of the activating element. The injection needle can protrude beyond the distal end of the injection device in the activating position of the activating element. In this position, the distal end is formed by the distal end of the housing and/or by the distal end of the activating element. When the activating element is situated in the activating position, the injection needle can protrude or be advanced far enough beyond the distal end of the injection device that the needle length which protrudes beyond the distal end of the injection device corresponds to the injection depth. The activating element is designed to be placed onto an injection location provided on the patient. When the placed injection device is pressed onto the injection location, the activating element is shifted from the initial position into the activating position, i.e. into the proximal position in this case; this can be thought of as activating the activating element. The activating element can be designed to indicate, to the mechanism for injecting the injection needle or delivering the product, i.e. for example to effect a mechanical switch, that the injection device has been properly placed onto the injection location and the needle injected. In some preferred embodiments, the activating element is a needle protecting or covering sleeve which can reduce access to the needle and therefore the danger of injury.

In some preferred embodiments, an injection device in accordance with the present invention also comprises a spring, such as a restoring spring, wherein the spring is coupled to the activating element such that the activating element can be shifted from the activating position into the end position using and/or by the spring. The spring can be a tension spring or a pressure spring. Plastics or metals, for example spring steel, are materials which may be considered for the spring. In some preferred embodiments, the spring is helical. Instead of a spring, other spring elements can also be used. The spring elements obey Hooke's Law, although this is not absolutely necessary for the injection device to function. The spring can be directly or indirectly coupled to the activating element. If directly coupled, the spring is supported on the activating element. In some preferred embodiments, the distal end of the spring is supported on the activating element, and the other end can be supported on an advancing member. If the spring is indirectly coupled to the activating element, the activating element can be coupled via an element which is connected to the activating element and on which the spring is supported. Such an element can, for example, be a transfer element. The activating element and the transfer element can be connected, axially fixed, to each other. In some embodiments, at least the activating element and the transfer element can respectively transfer a pressure force onto the other.

In some embodiments, the advancing member can be shifted relative to the housing in an advancing direction, e.g. an injection direction, a delivery direction or distal direction. In some embodiments, the spring is coupled to the advancing member such that it can be tensed when the advancing member moves in the advancing direction. By tensing the spring, the movement of the advancing member in the advancing direction increases the spring force and therefore the force which acts on the activating element, such that an increased force then acts on the activating element, whereas initially a small force acts on the activating element. The initially small force is desirable for activating the activating element, i.e. moving the activating element into its activating position and/or in the proximal direction. This keeps the spring force small as a portion of the total force required to activate the activating element, which can also include switching forces or frictional forces. The increased force after the advancing member has been shifted is desirable to move the activating element completely and reliably from its activating position into its end position. In some preferred embodiments, in its end position, the activating element is latched, axially fixed, relative to the housing. The increased spring force is likewise advantageous for establishing this latching connection, which can be established between the housing and the activating element, since it enables it to reliably latch in. The latching reduces the danger of injury even further, since the activating element is prevented from being inadvertently retracted, which would cause the injection needle to protrude.

In some embodiments, a device in accordance with the present invention also comprises another spring, an advancing spring for moving the advancing member in the advancing direction. The advancing spring can tense the spring of the activating element, which is then referred to as the restoring spring to better distinguish it. in some preferred embodiments, the advancing spring is biased heavily enough that it exhibits a greater spring force than the restoring spring. In some embodiments, the bias on the advancing spring should be selected such that the force of the advancing spring is greater than the force of the restoring spring in all the switching positions of the injection device.

In some embodiments, the injection device also comprises a product container generally associated with the housing. The product container can be formed by the housing itself or by a separate product container which is or can be inserted into the housing, e.g. an ampoule. At one end, the product container is or can be connected to the injection needle, e.g., the injection needle is or can be fastened directly to the product container. At the other end, the proximal end, the product container comprises an opening which is sealed by a piston which is arranged in the product container. The piston can be shifted relative to the product container to deliver product, such that the product situated between the piston and the opposite end of the product container is delivered due to the movement of the piston. The advancing member can be coupled to the piston which is arranged in the product container, such that the piston can be shifted relative to the housing of the injection device by the advancing member. The advancing member can thus act on the piston indirectly, such as via the product container or directly.

In some preferred embodiments, when the activating element moves from the initial position into the activating position or proximal position, the restoring spring can be tensed by a first distance, and when the advancing member moves in the distal direction from its initial position, such as for example its proximal position, the restoring spring can be tensed by a second distance, in addition to the first distance. In some preferred embodiments, the first distance is proportional to a first amount of change in the spring force, and the second distance is proportional to a second amount of change in the spring force. The force acting on the activating element thus amounts to at least the sum of the first amount and the second amount, wherein the original bias on the spring is also added.

In a preferred embodiment, the advancing member is a piston rod which need not necessarily be solid, but may be rather sleeve-shaped, i.e. at least partially hollow and/or cylindrical. The piston can be shifted relative to the product container using the advancing member. In some embodiments, the needle is injected manually into the patient. The advancing spring, which in this case is a delivery spring, can for example be supported on the housing or on an element which is fixed with respect to the housing, and on the piston rod. Furthermore, the restoring spring can be supported on the piston rod or on an element which is connected, axially fixed, to it, and on the activating element. This relaxes the delivery spring for advancing the piston during a product delivery, wherein the restoring spring is simultaneously tensed by the delivery spring. A triggering element can be provided which releases a blocking connection, which prevents the piston rod from moving in the delivery direction due to the biased delivery spring, such that a delivery movement can be performed. In some embodiments, the activating element has to be activated in addition to the triggering element to enable the blocking connection to be released. The elements are correspondingly coupled to each other.

In another preferred embodiment, the injection device is an auto-injector. The advancing member can be an advancing element using which the entire product container can be shifted relative to the housing. Shifting the product container in an injection direction, i.e. the distal (forward) direction, enables the injection needle to protrude from the distal end of the injection device to be injected into the patient. The product container can be shifted distally from an initial position into an end position. In the end position, the injection needle protrudes distally beyond the distal end of the injection device. In the initial position of the product container, the injection needle does not protrude beyond the distal end of the injection device, i.e. the distal end of the needle is situated proximally with respect to the distal end of the injection device.

In some embodiments, the advancing element can be shifted in the injection direction by the advancing spring which serves as an injection spring. The advancing element can charge the product container with an advancing force, at least in the distal direction. The product container can be held in a product container holder which can be moved together with the product container in the injection direction. In some preferred embodiments, the advancing spring is supported on the housing or on an element which is connected, axially fixed, to the housing, and on the advancing element or an element which is connected, axially fixed, to the advancing element. The advancing element is latched, axially fixed, relative to the housing in a position in which the product container is situated in its initial position. When this latching connection is released, the advancing element is released for an advancing movement. As long as the latching connection exists, the advancing spring is in a tensed state, wherein when the latching connection is released, the restoring spring can be relaxed and the advancing element thus moves in the advancing direction and simultaneously tenses the restoring spring by an amount, by the second amount. The latching connection by which the advancing element is held can be released when a triggering element such as a triggering button is activated, in combination with activating the activating sleeve, thus enabling the restoring spring to be biased by a first amount.

In some embodiments, the injection device comprises a piston rod which can be shifted relative to the advancing element. Furthermore, the piston can be able to be shifted by the piston rod relative to the product container. The injection device comprises a releasing member which can block, lock or prevent the relative movement between the piston rod and the advancing element. The releasing member blocks the relative movement between the piston rod and the advancing element during the injection movement. A switching ring can be provided which releases the releasing member at the end of the injection movement or moves it out of engagement with the piston rod or at least enables the releasing member to be released, such that the piston rod can perform a delivery movement. For advancing the piston rod, i.e. for the delivery movement, i.e. when the piston rod is to be moved relative to the advancing element, a delivery spring is provided which acts on the piston rod. The piston rod can be sleeve-shaped, wherein the delivery spring can be situated in the sleeve-shaped piston rod, in a biased state. The advancing spring can be supported on the piston rod and on an element which is fixed with respect to the housing or on the advancing element or on an element which is connected, axially fixed, to the advancing element.

In some embodiments, the present invention comprises a method for operating an injection device, wherein an advancing member for an injection movement and a product delivery is moved in the distal direction relative to a housing and thereby tenses a spring, e.g. a restoring spring, which acts on an activating element, wherein the activating element is shifted distally by the tensed spring from the proximal position into an end position.

BRIEF DESCRIPTION OF THE DRAWINGS

FIGS. 1A and 1B are sectional views of an embodiment of an injection device in accordance with the present invention in an initial position, wherein FIG. 1B is the view from FIG. 1A rotated about the longitudinal axis by 90°;

FIGS. 2A and 2B are sectional views of the injection device of FIGS. 1A and 1B, comprising an activating sleeve which is situated in an activating position, wherein FIG. 2B is the view from FIG. 2A rotated about the longitudinal axis by 90°;

FIGS. 3A and 3B are sectional view of the injection device of FIGS. 1A and 1B in an injection position, wherein FIG. 3B is the view from FIG. 3A rotated about the longitudinal axis by 90°.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1A:
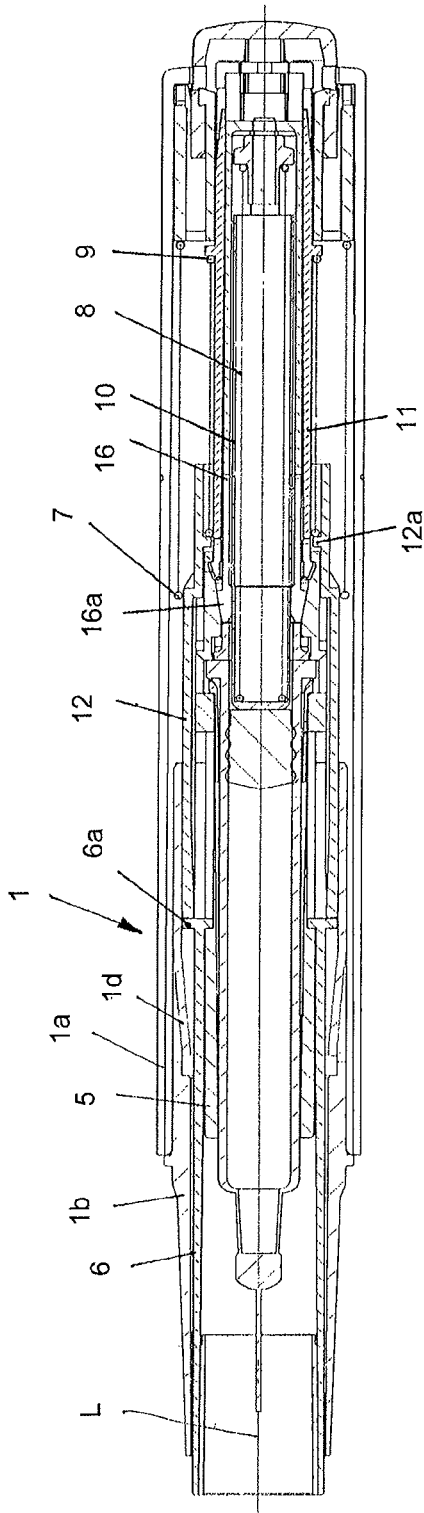
Figure 1B:
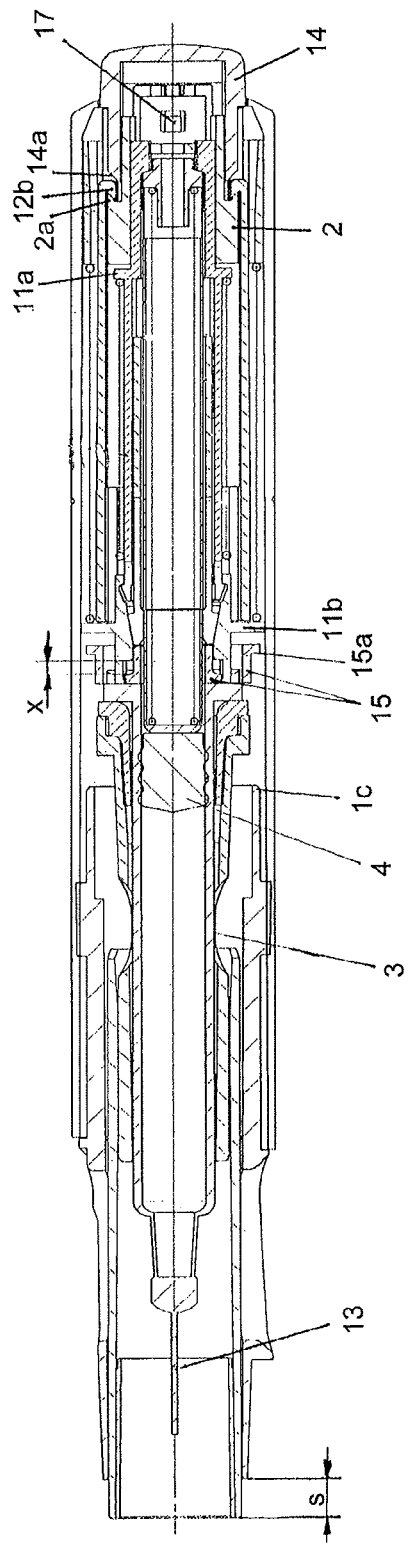

FIGS. 1A and 1B show an injection device which is embodied as an auto-injector. The injection device comprises a housing 1 which is formed from a distal housing part 1b and a proximal housing part 1a. The distal housing part 1b is latched, axially fixed, to the proximal housing part 1a and cannot be directly released by the user. Configuring the injection device in two parts has the advantage that easier assembling is possible. The distal housing part 1b, mounts (or carries) an activating element which is embodied as a needle protecting sleeve 6, such that it can be axially shifted, i.e. such that the needle protecting sleeve 6 can be shifted along the longitudinal axis L of the injection device. The injection device is shown in FIGS. 1A and 1B with a needle protecting sleeve 6 situated in its initial position. In the initial position, the needle protecting sleeve 6 protrudes beyond the distal end of the distal housing part 1b. As shown in this example, the needle protecting sleeve 6 protrudes by the amount "s". The distal end of an injection needle 13 which is surrounded by the housing 1 is situated proximally with respect to the distal end of the needle protecting sleeve 6 and, as shown in this case, also proximally with respect to the distal end of the distal housing part 1b. Thus, even when the needle protecting sleeve 6 is shifted in the proximal direction by the distance "s", the distal end of the injection needle 13 does not protrude beyond the distal end of the injection device (FIGS. 2A and 2B), i.e. in the activated position of the needle protecting sleeve 6, the tip of the injection needle is protected against being inadvertently accessed.

The needle protecting sleeve 6 is designed to be placed onto an injection location on a patient. When the placed injection device is pressed onto the patient, the needle protecting sleeve 6 is activated, i.e. shifted in the proximal direction, wherein a transfer element 12 which abuts the proximal end of the needle protecting sleeve 6 is slaved by the same distance "s" as the distance by which the needle protecting sleeve 6 is shifted, and is therefore likewise moved relative to the housing 1.

A collar 12a which protrudes radially inward and on which the distal end of a spring 9 is supported is formed on the transfer element 12. The proximal end of the spring 9 is supported on a collar 11a which points radially outward and is formed on an advancing element 11 which serves as the advancing member. Thus, when the needle protecting sleeve 6 is moved into its activating position, the spring 9 is biased by a first amount by the movement of the transfer element 12 by the first distance. If, for example, the needle protecting sleeve 6 is moved in the proximal direction by the distance "s", then the spring 9 is biased by an amount which is dependent on the distance "s". The resultant spring force may be ascertained using Hooke's Law.

When the user removes the injection device from the injection location, the needle protecting sleeve 6 is retracted by the spring 9 back into its initial position, as shown for example in FIGS. 1A and 1B, since an injection movement has not yet been performed.

Figures 2A, 2B:
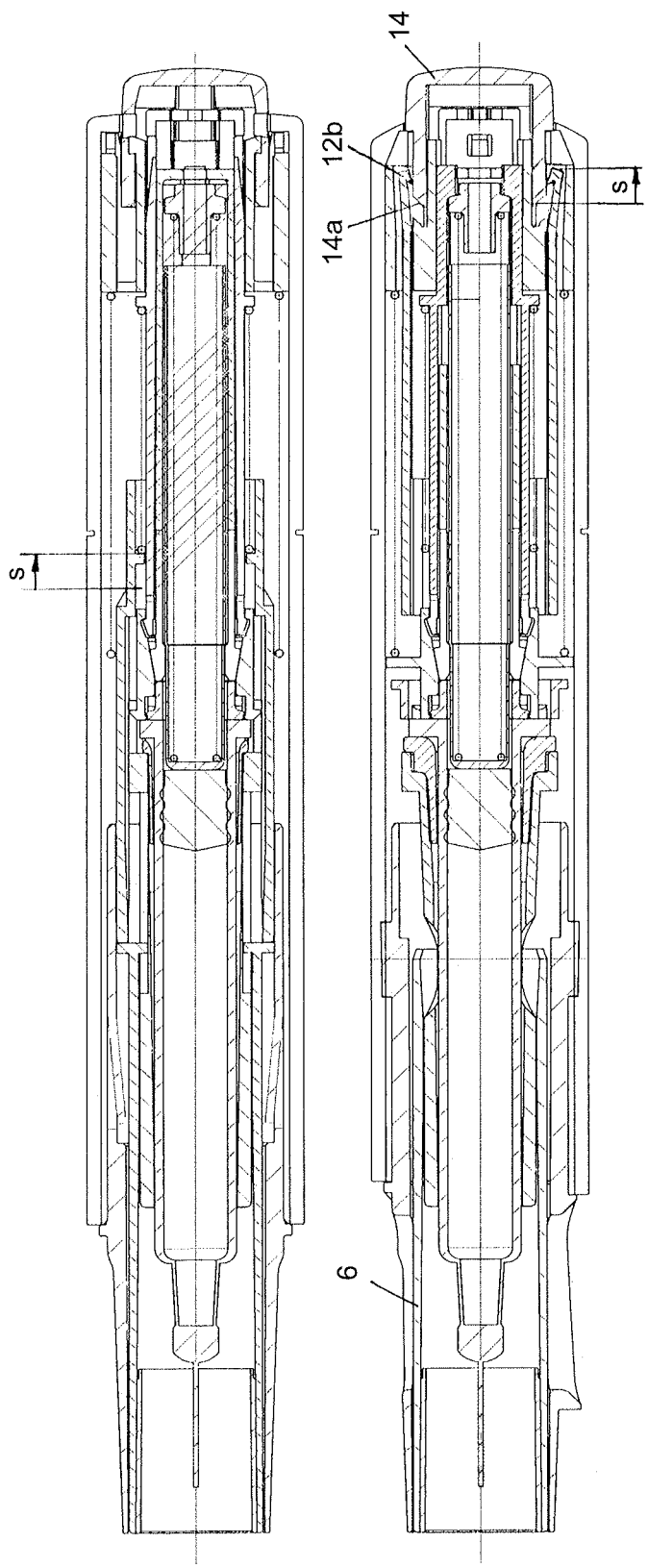

The proximal end of the transfer element 12 comprises a blocking member 12b which engages with a blocking groove and thus prevents the needle protecting sleeve 6 from moving any further in the distal direction than as shown in FIGS. 1A and 1B. The blocking groove is distally restricted by an element which is fixed with respect to the housing, e.g. a cage 2, and proximally restricted by a cam surface 14a which is formed by a triggering element 14. The triggering element 14 serves to trigger the injection device to administer the product. In the position shown in FIG. 1B, the triggering element 14 cannot be pressed, since the cage 2 comprises an undercut 2a which prevents the blocking member 12b from unlatching by moving radially outward. The cam surface 14a cannot therefore press the blocking member 12b radially outward, out of the blocking groove, despite exerting a pressure on the triggering element 14. If the needle protecting sleeve 6 as shown in FIGS. 2A and 2B is moved in the proximal direction by the distance "s", the blocking member 12b is also moved in the proximal direction and is thus pressed radially outward, out of the blocking groove, by the cam surface 14a of the triggering element 14. The triggering element 14 is thus released for a triggering movement, i.e. for a movement in the distal direction. When the triggering element 14 is moved in the triggering direction, a snap-on connection 17—which prevents the advancing element 11 from moving in the distal direction, i.e. in the injection direction—is released, such that the advancing element 11 can be moved in the injection direction. Once the triggering element 14 has been activated, it latches—axially fixed—to the cage 2, as shown in FIG. 3B, and alternatively to the housing 1, such that the blocking groove for the blocking member 12b is sufficiently closed that the blocking member 12b can no longer latch in between the cam surface 14a and the undercut 2a.

Since the advancing element 11 is released for a movement in the distal direction after the triggering element 14 has been activated, a biased injection spring 7 which serves as the advancing spring can move the advancing element 11 in the delivery direction. The advancing element 11 is latched, axially fixed, to a supporting element 11b, such that the two parts behave as a single part. The division into two parts may be expedient for assembling reasons. The distal end of the advancing spring 7 is supported on a collar which points radially outward and is formed on the supporting element 11b, and the proximal end of the advancing spring 7 is supported on the cage 2. The advancing spring 7 surrounds the transfer element 12 and the advancing element 11, as shown for example in FIG. 1B. Driven by the advancing spring 7, the advancing element 11 is moved in the delivery direction together with a piston rod 10 accommodated in it, wherein the spring 9 is tensed by a second amount which is dependent on the distance "u", in addition to the first amount which is dependent on the distance "s". This increases the spring force of the spring 9.

The advancing element 11 is coupled to a product container 3 via the supporting element 11b, such that when moving in the delivery direction, it can likewise slave the product container 3 in the delivery direction. In particular, the distal end of the supporting element 11b abuts the proximal end of the product container 3. The product container 3 is held in a product container holder 5. The product container 3 is held axially fixed relative to the product container holder 5. The product container holder 5 serves as an axial guide for the product container 3. The injection needle 13 is fastened to the distal end of the product container 3. The injection needle 13 is fluidically connected to the interior of the product container 3. A piston 4 is arranged at the proximal end of the product container 3 and can be moved relative to the product container 3. When the piston 4 is moved in the direction of the injection needle 13, the product is delivered through the injection needle 13.

Figures 3A, 3B:
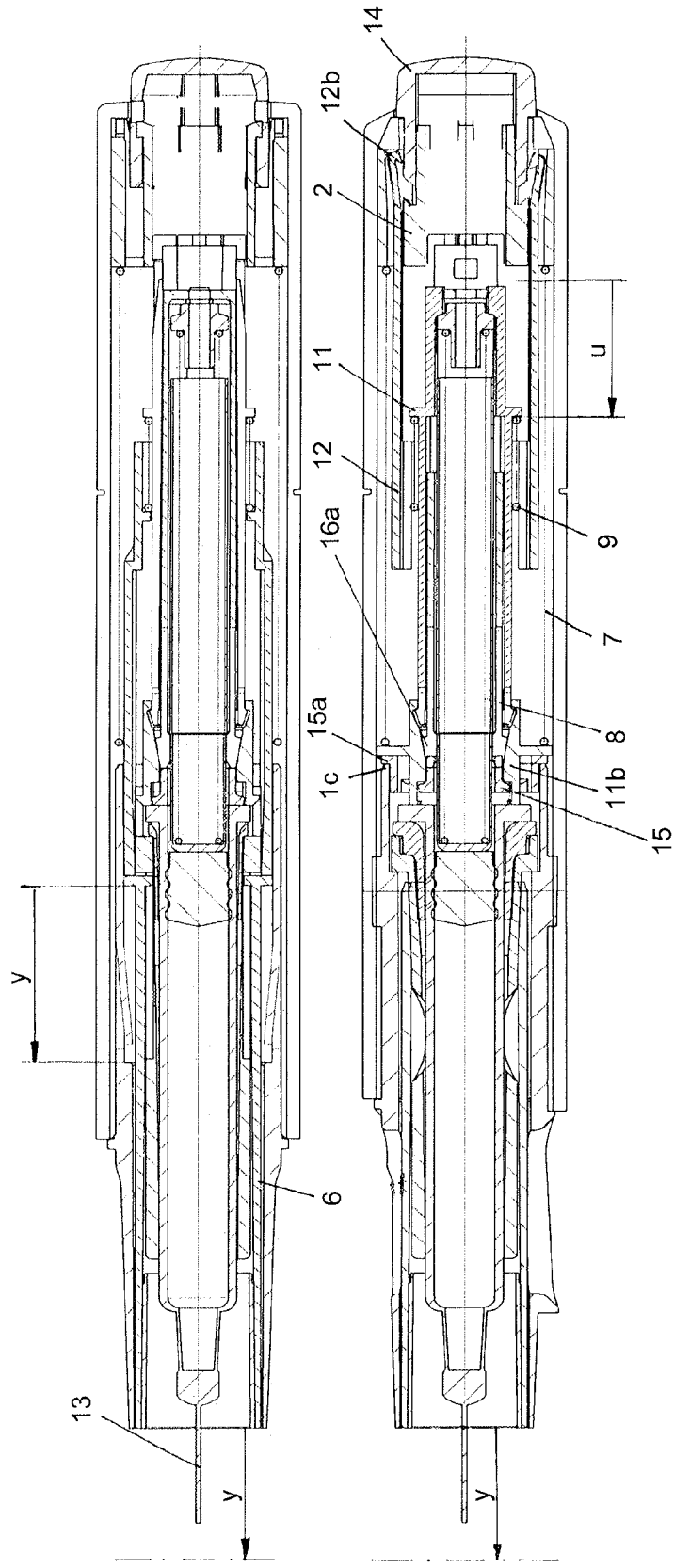

During the injection movement of the advancing member 11, the product container 3 and therefore the injection needle 13 is shifted in the distal direction, wherein the injection needle 13 protrudes distally beyond the distal end of the injection device, as shown in FIGS. 3A and 3B. The distance which the injection needle 13 protrudes corresponds to the injection depth into the tissue of the patient.

Before an injection movement has been completely performed, the piston rod 10 which is surrounded by the advancing element 11 is connected, axially fixed, to the advancing element 11. This means that the piston rod 10 participates in the advancing movement of the advancing element 11, wherein no relative movement between the advancing element 11 and the piston rod 10 is performed. The releasing member 16a is responsible for arranging the piston rod 10 axially fixed relative to the advancing element 11. The releasing member 16a is formed on a functional sleeve 16 which is arranged between the piston rod 10 and the advancing element 11. The releasing member 16a is elastically connected to the functional sleeve 16 via an elastic arm or integrally formed with it. In the switching positions shown in FIGS. 1A, 1B, 2A and 2B, a protrusion of the releasing member 16a which is directed radially inward engages with a collar or heel which is circumferentially formed on the outer surface of the piston rod 10. This prevents the piston rod 10 from moving in the distal direction relative to the advancing element 11. The side of the releasing member 16a which points radially outward exhibits a conical surface which co-operates with a correspondingly counteracting conical surface of the supporting element 11b which is directed radially inward. The surface of the supporting element 11b which is directed radially inward prevents the releasing member 16a from unlatching from the engagement with the piston rod 10, by preventing the releasing member 16a from moving outward in the radial direction.

The injection device also features a switching element 15 which can be moved relative to the supporting element 11b by a distance "x", as shown in FIG. 1B. The switching element 15 comprises an abutment surface 15a which can be moved into axial abutment with an abutment 1c formed by the housing 1, e.g. by the distal housing part 1b. At the end of the injection movement, the switching element 15 is pressed against the abutment 1c by the injection spring 7. This holds the switching element 15 axially fixed with respect to the housing 1, while the injection spring 7 slides the supporting element 11b further in the distal direction, thus shifting the supporting element 11b relative the switching element 15 by the distance "x", i.e. by a switching distance. FIG. 3B shows the position of the supporting element 11b and the switching element 15 relative to each other. As likewise shown in FIG. 3B, there is then a radial gap between the supporting element 11b and the releasing member 16a, such that the releasing member 16a can unlatch, radially outwardly, from the engagement with the piston rod 10. The piston rod 10 is then released for a movement in the delivery direction, i.e. the distal direction.

The piston rod 10 is formed as a sleeve in which a delivery spring 8 is arranged for driving the piston rod 10 relative to the advancing element 11 and/or for a product delivery. The distal end of the delivery spring 8 is supported on a distally formed end-facing surface of the piston rod 10, and the proximal end of the delivery spring 8 is supported on the advancing element 11 or an element which is formed, axially fixed, with the advancing element 11, or alternatively on the functional sleeve 16 or on an element which is formed axially fixed with respect to the functional sleeve 16. After the piston rod 10 has been released, e.g. after an injection movement has been completely performed, the biased delivery spring 8 drives the piston rod 10 in the delivery direction. The distal end of the piston rod 10 acts on the piston 4, such that it is slaved in the distal direction and causes the product to be delivered.

In some preferred embodiments, the springs described herein are pressure springs and embodied to be helical. The springs are in particular made of a suitable metallic material, e.g. spring steel, a plastic, etc. The injection spring 7 is biased and/or selected such that in its most relaxed state, it exhibits a spring force which is greater than or at least as great as the spring 9 in its most tensed state, in some preferred embodiments, after it has been biased by the first amount and the second amount.

After the product has been successfully delivered (not shown in the figures), the user of the device removes the injection device from the injection location. This then shifts the needle protecting sleeve 6 in the distal direction, due to the spring 9 which is biased by the first distance "s" and the second distance "u", with a force which is greater than the force which was required to shift the needle protecting sleeve 6 by the distance "s" from the position shown in FIG. 1B into the position shown in FIG. 2B. Since the blocking groove between the cage 2 and the triggering element 14 for latching in the blocking member 12b is then sealed (see FIG. 3B), the transfer element 12 and therefore also the needle protecting sleeve 6 can be shifted in the distal direction by a distance which is greater than the distance "s" by which the needle protecting sleeve 6 was shifted in the proximal direction from the position shown in FIG. 1B. The needle protecting sleeve 6 is shifted far enough in the distal direction that its distal end protrudes distally beyond the distal end of the injection needle 13. In this respect, it is preferred in some embodiments if, as shown in FIG. 3A, a gap "y" between a locking cam 6a formed radially outward on the needle protecting sleeve 6 and an axial abutment formed by the housing 1, e.g. by the distal housing part 1b, is correspondingly selected. When the needle protecting sleeve 6 moves in the distal direction, the locking cam 6a abuts the axial abutment formed by the housing 1. In this position, the needle protecting sleeve 6 is situated in its end position in which it completely covers the injection needle 13. When the locking cam 6a moves by the distance "y", it crosses a locking tongue 1d formed by the housing 1, e.g. by the distal housing part 1b. The locking tongue 1d can spring radially outward and is integrally formed on the distal housing part 1b. Once the locking cam 6a has crossed the locking tongue 1d, the locking tongue 1d springs radially inward, such that its distal abutment surface is braced against the proximal side of the locking cam 6a. The needle protecting sleeve 6 is then blocked against moving in the proximal direction, such that the needle 13 can no longer be released. In other words, the needle protecting sleeve 6 latches, axially fixed, to the housing 1. The needle protecting sleeve 6 serves as a needle protection and reduces the danger of injury to persons handling the injection device. The used injection device can then be securely disposed of.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising:
   a) a housing enclosing a product container connected to an injection needle;
   b) an activating element shiftable relative to the housing from an initial position in which the activating element protects the injection needle to a proximal position to permit manual injection of the injection needle;
   (c) an advancing member shiftable relative to the housing in an advancing direction, said advancing member comprising a hollow piston rod with a delivery spring fixed thereon, said piston rod acting on a piston to shift it relative to the product container;
   d) a restoring spring for shifting the activating element distally from the proximal position to an end position; wherein
   e) the restoring spring has one end supported on the activating element and another end supported on an element connected to the piston rod, such that the restoring spring is tensed by a first amount when the activating element moves from the initial position to the proximal position, and the movement of the advancing member in the advancing direction, driven by relaxation of the delivery spring, simultaneously advances the piston rod for product delivery and moves the element connected to the piston rod in a direction that increases the tension in the restoring spring to cause a force greater than the force initially acting on the activating element.

2. The injection device according to claim 1, wherein in its end position, the activating element protrudes distally beyond a distal end of the housing.

3. The injection device according to claim 1, wherein the activating element is a needle protecting sleeve which in its end position protrudes beyond the distal end of an injection needle carried by the injection device.

4. The injection device according to claim 1, wherein the activating element is moveable in the proximal direction from the initial position, in which the activating element protrudes distally beyond the distal end of the housing, to the proximal position which comprises an activating position.

5. The injection device according to claim 4, wherein the restoring spring is tensed by a second amount based on a distance the advancing member moves in the advancing direction from an initial position.

6. The injection device according to claim 5, wherein in its end position, the activating element protrudes distally beyond the distal end of the housing by a greater amount than in its initial position.

7. The injection device according to claim 1, wherein in its end position, the activating element is latched, axially fixed, relative to the housing.

8. The injection device according to claim 1, wherein the piston arranged in the product container can be shifted relative to the housing by the advancing member.

9. The injection device according to claim 8, wherein the advancing member comprises an advancing element by which the product container can be shifted relative to the housing.

10. The injection device according to claim 9, wherein the product container can be shifted distally from an initial position into an end position, wherein in the end position, the injection needle arranged on the product container protrudes distally beyond the distal end of the injection device.

11. The injection device according to claim 10, wherein the piston rod can be shifted relative to the advancing element.

12. The injection device according to claim 11, further comprising a releasing member which can block the relative movement between the piston rod and the advancing element.

13. A method for operating an injection device, said device comprising:

a) a housing enclosing a product container connected to an injection needle;
b) an activating element shiftable relative to the housing from an initial position to a proximal position to permit manual injection of the injection needle;
(c) an advancing member shiftable relative to the housing in an advancing direction, said advancing member comprising a hollow piston rod with a delivery spring fixed thereon, said piston rod acting on a piston to shift it relative to the product container;
d) a restoring spring for shifting the activating element distally from the proximal position to an end position; wherein
e) the restoring spring has one end supported on the activating element and another end supported on an element connected to the piston rod, such that the restoring spring is tensed by a first amount when the activating element moves from the initial position to the proximal position,
wherein the delivery spring shifts the advancing member for product injection movement or a product delivery in an advancing direction relative to a housing and thereby simultaneously tenses the restoring spring to increase the tension in the restoring spring to cause a force greater than the force initially acting on the activating element, wherein the activating element is shifted by the tensed spring from an activating position into an end position.

14. The method of claim 13, wherein when the activating element is shifted by the tensed spring into an end position, it is latched, axially fixed, relative to the housing.

15. The method of claim 13 wherein the activating element is a needle protecting sleeve.

16. The method of claim 13 further comprising, pressing the injection device against the patient activates the needle protecting sleeve to enable manual injection of the needle.

17. The method of claim 13 further comprising, activating a triggering element to release a blocking connection that prevents the piston rod from moving in a delivery direction.

* * * * *